United States Patent
Murata

(10) Patent No.: US 8,815,959 B2
(45) Date of Patent: Aug. 26, 2014

(54) OIL-IN-WATER EMULSION COMPOSITION AND METHOD FOR PRODUCING SAME

(75) Inventor: Takeshi Murata, Odawara (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 13/702,484

(22) PCT Filed: Jun. 3, 2011

(86) PCT No.: PCT/JP2011/062787
§ 371 (c)(1),
(2), (4) Date: Dec. 6, 2012

(87) PCT Pub. No.: WO2011/155404
PCT Pub. Date: Dec. 15, 2011

(65) Prior Publication Data
US 2013/0102688 A1  Apr. 25, 2013

(30) Foreign Application Priority Data
Jun. 7, 2010 (JP) ................................. 2010-129674

(51) Int. Cl.
| | | |
|---|---|---|
| B01F 3/08 | (2006.01) |
| A61K 47/10 | (2006.01) |
| A61K 8/39 | (2006.01) |
| A61Q 19/00 | (2006.01) |
| A61K 8/34 | (2006.01) |
| A61K 8/81 | (2006.01) |
| B01F 17/00 | (2006.01) |
| A61K 8/06 | (2006.01) |
| A61K 9/107 | (2006.01) |

(52) U.S. Cl.
CPC . *A61K 47/10* (2013.01); *A61K 8/39* (2013.01); *A61Q 19/00* (2013.01); *A61K 8/345* (2013.01); *A61K 8/8152* (2013.01); *B01F 17/0021* (2013.01); *A61K 8/062* (2013.01); *A61K 2800/52* (2013.01); *A61K 9/107* (2013.01); *B01F 17/0085* (2013.01); *A63K 2800/10* (2013.01)
USPC .......... 516/76; 525/54.21; 525/187; 525/403; 525/404; 525/408

(58) Field of Classification Search
CPC ....... C07C 43/04; C07C 43/14; B01F 3/0803; B01F 3/0811; B01F 2003/0842; C08J 3/07; C08G 65/2609; C08G 65/2615; C08G 65/3312
USPC .......... 516/76; 525/54.21, 187, 403, 404, 408
See application file for complete search history.

(56) References Cited

U.S. PATENT DOCUMENTS

| | | | |
|---|---|---|---|
| 3,146,059 A | 8/1964 | Suzuki et al. | |
| 6,090,395 A | 7/2000 | Asmus et al. | |
| 6,375,960 B1 * | 4/2002 | Simonnet et al. | 424/401 |
| 6,534,069 B1 | 3/2003 | Asmus et al. | |
| 2002/0160029 A1 | 10/2002 | Asmus et al. | |
| 2004/0071748 A1 | 4/2004 | Asmus et al. | |
| 2006/0121071 A1 | 6/2006 | Asmus et al. | |
| 2006/0172059 A1 | 8/2006 | Takeuchi et al. | |
| 2006/0263396 A1 | 11/2006 | Asmus et al. | |
| 2010/0331422 A1 | 12/2010 | Asmus et al. | |

FOREIGN PATENT DOCUMENTS

| | | |
|---|---|---|
| JP | 49 121788 | 11/1974 |
| JP | 1 266844 | 10/1989 |
| JP | 11 508253 | 7/1999 |
| JP | 2000 265098 | 9/2000 |
| JP | 2001 181543 | 7/2001 |
| JP | 2003 321321 | 11/2003 |
| JP | 2009 249325 | 10/2009 |
| JP | 2011 231043 | 11/2011 |
| JP | 2011 246398 | 12/2011 |
| JP | 2012 1527 | 1/2012 |
| TW | 570807 B | 1/2004 |
| TW | 201006501 A1 | 2/2010 |
| TW | I324506 B | 5/2010 |
| WO | 2004 056216 | 7/2004 |

OTHER PUBLICATIONS

International Search Report Issued Aug. 16, 2011 in PCT/JP11/062787 Filed Jun. 3, 2011.
U.S. Appl. No. 13/700,322, filed Nov. 27, 2012, Murata.
U.S. Appl. No. 13/643,801, filed Oct. 26, 2012, Murata.

* cited by examiner

*Primary Examiner* — Robert Jones, Jr.
(74) *Attorney, Agent, or Firm* — Oblon, Spivak, McClelland, Maier & Neustadt, L.L.P.

(57) ABSTRACT

There is provided an oil-in-water emulsion composition whose continuous phase is an aqueous phase, but which has a high moisture evaporation suppressing effect and is also superior in feeling, and a method for producing the same.
An oil-in-water emulsion composition containing an oily component having an inorganic value of 2500 or less, an organic value of 5000 or less and an IOB value of 0.3 to 0.5, the oil-in-water emulsion composition containing the following components (A) to (C) in an aqueous phase.
(A) a polyoxyethylene alkyl or alkenyl ether having alkyl group or alkenyl group having 20 to 24 carbon atoms and an average molar number of ethylene oxide added of 1.5 to 4
(B) a polyhydric alcohol
(C) a water-soluble polymer.

14 Claims, No Drawings

OIL-IN-WATER EMULSION COMPOSITION AND METHOD FOR PRODUCING SAME

CROSS REFERENCE TO RELATED APPLICATION

This application is a 371 of PCT/JP2011/062787, filed on Jun. 3, 2011, and claims priority to Japanese Patent Application No. 2010-129674, filed on Jun. 7, 2010.

FIELD OF THE INVENTION

The present invention relates to an oil-in-water emulsion composition which has a high water evaporation inhibiting effect and is also superior in a feeling upon use, and to a method for producing the oil-in-water emulsion composition.

BACKGROUND OF THE INVENTION

In the fields of cosmetics, drugs, quasi drugs, foods, etc., there are many compositions containing water as a base. Such aqueous compositions are often stored in closed containers to prevent evaporation of water from the compositions. However, water may be gradually evaporated from aqueous compositions due to the reasons such as opening of a lid in daily use, resulting in a change of physical properties and color. In spray containers, pump containers and the like, the discharged content remains at the discharge opening and is dried near the discharge opening, and thus the content adhered to the discharge opening results in a change of color and odor, which makes a feeling upon use worsened, disadvantageously. Further, the content is dried and solidified, causes clogging, and cannot be discharged in some cases, disadvantageously.

In order to suppress such solidification of the content and prevent such clogging of the discharge containers, it has been proposed to blend a non-volatile liquid oil with one or more selected from a substances that are solid at 25° C. or less and/or a coating-forming polymer, at a specific ratio (see Patent Document 1). However, a large amount of the non-volatile oil is necessarily blended in order to suppress solidification of the content, which limits possible formulations. Even if the non-volatile oil is added at a specific ratio, the content is solidified and clogging is not sufficiently prevented.

On the other hand, it has been proposed to improve long-term stability of an emulsion containing a high concentration of alcohol by blending polyoxyethylene behenyl ether having an average number of ethylene oxide added of 5 or more into the emulsion composition (see Patent Documents 2 and 3). Such a method, however, intends to prevent decreases in hardness and viscosity of the emulsion, and effects on water are not known at all.

PRIOR ART LIST

Patent Document

[Patent Document 1] JP-A-2003-321321
[Patent Document 2] JP-A-01-266844
[Patent Document 3] JP-A-11-508253

SUMMARY OF THE INVENTION

The present invention relates to an oil-in-water emulsion composition containing an oily component having an inorganic value of 2500 or less, an organic value of 5000 or less and an IOB value of 0.3 to 0.5, the oil-in-water emulsion composition containing the following components (A) to (C) in the aqueous phase.
(A) a polyoxyethylene alkyl or alkenyl ether having an alkyl or alkenyl group having 20 to 24 carbon atoms and an average molar number of ethylene oxide added of 1.5 to 4
(B) a polyol
(C) a water-soluble polymer The present invention also relates to a method for producing an oil-in-water emulsion composition, including forming an oil-in-water emulsion composition containing a water-soluble polymer, and mixing a composition containing the following components (A) and (B) with the oil-in-water emulsion composition at a temperature of 45° C. or less.
(A) a polyoxyethylene alkyl or alkenyl ether having an alkyl or alkenyl group having 20 to 24 carbon atoms and an average molar number of ethylene oxide added of 1.5 to 4
(B) a polyol

EMBODIMENTS FOR CARRYING OUT THE INVENTION

As a result of investigation of components which can inhibit water evaporation from aqueous compositions, the present inventors have found that moisture evaporation from aqueous compositions can be significantly suppressed using a water-soluble polymer and a polyoxyethylene alkyl or alkenyl ether in combination and that such an effect is particularly superior when using a polyoxyethylene alkyl or alkenyl ether having alkyl group or alkenyl group having 20 to 24 carbon atoms and an average molar number of ethylene oxide added of 1.5 to 4, and the inventors have previously filed a patent application (JP-2010-102160).

However, it has been found that when a polyoxyethylene alkyl or alkenyl ether having alkyl group or alkenyl group having 20 to 24 carbon atoms and an average molar number of ethylene oxide added of 1.5 to 4 is emulsified together with a specific oil, the polyoxyethylene alkyl or alkenyl ether having alkyl group or alkenyl group having 20 to 24 carbon atoms and an average molar number of ethylene oxide added of 1.5 to 4 is dissolved in the oil and the water evaporation inhibiting effect of the aqueous phase is decreased, disadvantageously.

Accordingly, the present invention relates to a provision of an oil-in-water emulsion cosmetic which is an oil-in-water emulsion composition, but has a high water-evaporation-inhibiting effect and is also superior in a feeling upon use, and a method for producing the same.

As a result of studies to achieve the above advantage of the present invention, the present inventors have found that water evaporation from the aqueous phase may be suppressed and a superior feeling upon use may be provided even in oil-in-water emulsion compositions by adding a polyoxyethylene alkyl or alkenyl ether having alkyl group or alkenyl group having 20 to 24 carbon atoms and an average molar number of ethylene oxide added of 1.5 to 4, a water-soluble polymer and a polyol to the aqueous phase to form a dispersion. This finding has led to the completion of the present invention.

The oil-in-water emulsion composition of the present invention has a high water-evaporation-inhibiting effect, may suppress a change in appearance, such as separation, even if it is stored for a long time, and has superior stability over time. Because such a high water-evaporation-inhibiting effect is exhibited by addition of a small amount of the polyoxyethylene alkyl or alkenyl ether (A), the formulation is not limited and a feeling upon use is also not affected.

Preferred embodiments of the present invention are as follows, for example.

[1] An oil-in-water emulsion composition containing an oily component having an inorganic value of 2500 or less, an organic value of 5000 or less and an IOB value of 0.3 to 0.5, the oil-in-water emulsion composition containing the following components (A) to (C) in an aqueous phase.
(A) a polyoxyethylene alkyl or alkenyl ether having alkyl group or alkenyl group having 20 to 24 carbon atoms and an average molar number of ethylene oxide added of 1.5 to 4
(B) a polyol
(C) a water-soluble polymer

[2] A method for producing an oil-in-water emulsion composition, including forming an oil-in-water emulsion composition containing a water-soluble polymer, and mixing a composition containing the following components (A) and (B) with the oil-in-water emulsion composition at a temperature of 45° C. or less.
(A) a polyoxyethylene alkyl or alkenyl ether having alkyl group or alkenyl group having 20 to 24 carbon atoms and an average molar number of ethylene oxide added of 1.5 to 4
(B) a polyol

[3] The oil-in-water emulsion composition according to [1] or the production method according to [2], wherein the component (A) is a polyoxyethylene alkyl or alkenyl ether having alkyl group or alkenyl group having 20 to 24 carbon atoms and an average molar number of ethylene oxide added of 1.5 to 3.

[4] The oil-in-water emulsion composition according to [1] or [3] or the production method according to [2] or [3], wherein the component (A) is a polyoxyethylene alkyl or alkenyl ether having alkyl group or alkenyl group having 20 to 24 carbon atoms and an average molar number of ethylene oxide added of 1.5 to 2.5.

[5] The oil-in-water emulsion composition according to any one of [1], [3] and [4] or the production method according to any one of [2], [3] and [4], wherein the component (A) is selected from the group consisting of polyoxyethylene (2) arachyl ether, polyoxyethylene (3) arachyl ether, polyoxyethylene (4) arachyl ether, polyoxyethylene (2) behenyl ether, polyoxyethylene (3) behenyl ether, polyoxyethylene (4) behenyl ether, polyoxyethylene (2) carnaubyl ether, polyoxyethylene (3) carnaubyl ether and polyoxyethylene (4) carnaubyl ether.

[6] The oil-in-water emulsion composition according to any one of [1] and [3] to [5] or the production method according to any one of [2] and [3] to [5], wherein the component (A) is a polyoxyethylene alkyl or alkenyl ether having alkyl group or alkenyl group having 21 to 23 carbon atoms and an average molar number of ethylene oxide added of 1.5 to 4.

[7] The oil-in-water emulsion composition according to any one of [1] and [3] to [6] or the production method according to any one of [2] and [3] to [6], wherein the component (A) is a polyoxyethylene alkyl or alkenyl ether having alkyl group or alkenyl group having 21 to 23 carbon atoms and an average molar number of ethylene oxide added of 1.5 to 3.

[8] The oil-in-water emulsion composition according to any one of [1] and [3] to [7] or the production method according to any one of [2] and [3] to [7], wherein the component (A) is a polyoxyethylene alkyl or alkenyl ether having alkyl group or alkenyl group having 21 to 23 carbon atoms and an average molar number of ethylene oxide added of 1.5 to 2.5.

[9] The oil-in-water emulsion composition according to any one of [1] and [3] to [8] or the production method according to any one of [2] and [3] to [8], wherein the component (A) is polyoxyethylene (2) behenyl ether.

[10] The oil-in-water emulsion composition according to any one of [1] and [3] to [9] or the production method according to any one of [2] and [3] to [9], containing 0.05 to 20 mass % of the component (A) based on the total amount of the composition.

[11] The oil-in-water emulsion composition according to any one of [1] and [3] to [10] or the production method according to any one of [2] and [3] to [10], containing 0.1 to 20 mass % of the component (A) based on the total amount of the composition.

[12] The oil-in-water emulsion composition according to any one of [1] and [3] to [11] or the production method according to any one of [2] and [3] to [11], containing 0.1 to 10 mass % of the component (A) based on the total amount of the composition.

[13] The oil-in-water emulsion composition according to any one of [1] and [3] to [12] or the production method according to any one of [2] and [3] to [12], wherein the polyol (B) is one or more selected from the group consisting of a glycol, glycerin, diglycerin and polyglycerin.

[14] The oil-in-water emulsion composition according to any one of [1] and [3] to [13] or the production method according to any one of [2] and [3] to [13], wherein the polyol (B) is one or more selected from the group consisting of ethylene glycol, diethylene glycol, triethylene glycol, polyethylene glycol (average molecular mass: less than 650), propylene glycol, dipropylene glycol, polypropylene glycol (average molecular mass: less than 650), isoprene glycol, 1,3-butylene glycol, glycerin, diglycerin and polyglycerin.

[15] The oil-in-water emulsion composition according to any one of [1] and [3] to [14] or the production method according to any one of [2] and [3] to [14], wherein the polyol (B) is one or more selected from the group consisting of ethylene glycol, diethylene glycol, propylene glycol, dipropylene glycol and 1,3-butylene glycol.

[16] The oil-in-water emulsion composition according to any one of [1] and [3] to [15] or the production method according to any one of [2] and [3] to [15], containing the component (B) at a mass ratio of the component (B) to the component (A) of 0.5 to 50.

[17] The oil-in-water emulsion composition according to any one of [1] and [3] to [16] or the production method according to any one of [2] and [3] to [16], containing the component (B) at a mass ratio of the component (B) to the component (A) of 1 to 35.

[18] The oil-in-water emulsion composition according to any one of [1] and [3] to [17] or the production method according to any one of [2] and [3] to [17], containing the component (B) at a mass ratio of the component (B) to the component (A) of 1 to 20.

[19] The oil-in-water emulsion composition according to any one of [1] and [3] to [18] or the production method according to any one of [2] and [3] to [18], wherein the water-soluble polymer is one or more selected from the group consisting of a carboxyvinyl polymer, an alkyl acrylate-methacrylate copolymer, xanthan gum, hydroxypropylmethylcellulose, polyacrylamide and a (sodium acrylate/sodium acryloyldimethyltaurate) copolymer.

[20] The oil-in-water emulsion composition according to any one of [1] and [3] to [19] or the production method according to any one of [2] and [3] to [19], containing 0.01 to 5 mass % of the water-soluble polymer based on the total amount of the composition.

[21] The oil-in-water emulsion composition according to any one of [1] and [3] to [20] or the production method according to any one of [2] and [3] to [20], containing 0.05 to 3 mass % of the water-soluble polymer based on the total amount of the composition.

[22] The oil-in-water emulsion composition according to any one of [1] and [3] to [21] or the production method according to any one of [2] and [3] to [21], wherein the oily component, or an oily component in an oil phase, is an oily component having an inorganic value of 1500 or less, an organic value of 3000 or less and an IOB value of 0.3 to 0.5.

[23] The oil-in-water emulsion composition according to any one of [1] and [3] to [22] or the production method according to any one of [2] and [3] to [22], wherein the oily component, or the oily component in the oil phase, is an oily component having an inorganic value of 100 to 300, an organic value of 200 to 700 and an IOB value of 0.3 to 0.5.

[24] The oil-in-water emulsion composition according to any one of [1] and [3] to [23] or the production method according to any one of [2] and [3] to [23], wherein the oily component, or the oily component in the oil phase, is one or more selected from the group consisting of propylene glycol isostearate (inorganic value: 166, organic value: 410, IOB value: 0.4), propylene glycol oleate (inorganic value: 162, organic value: 420, IOB value: 0.39), ethylene glycol dioctanoate (inorganic value: 120, organic value: 340, IOB value: 0.35), diethylene glycol dicaprate (inorganic value: 195, organic value: 480, IOB value: 0.41), propylene glycol dicaproate (inorganic value: 120, organic value: 300, IOB value: 0.4), glyceryl dimyristate (inorganic value: 220, organic value: 620, IOB value: 0.35), glyceryl di(coconut oil fatty acid) (inorganic value: 220, organic value: 540, IOB value: 0.41), glyceryl dilaurate (inorganic value: 220, organic value: 540, IOB value: 0.41), diethylene glycol dilaurate (inorganic value: 195, organic value: 560, IOB value: 0.35), polyethylene glycol dilaurate (inorganic value: 270, organic value: 600, IOB value: 0.45), glyceryl monostearate diacetate (inorganic value: 180, organic value: 500, IOB value: 0.36), glyceryl sesquioleate (inorganic value: 243, organic value: 600, IOB value: 0.41), diisopropyl sebacate (inorganic value: 120, organic value: 300, IOB value: 0.4), diethyl sebacate (inorganic value: 120, organic value: 280, IOB value: 0.43), glyceryl tri(caprylate/caprate) (inorganic value: 180, organic value: 540, IOB value: 0.33), glyceryl tri(2-ethylhexanoate) (inorganic value: 180, organic value: 510, IOB value: 0.35), trimethylolpropane trioctanoate (inorganic value: 180, organic value: 550, IOB value: 0.33), glyceryl tricaprylate (inorganic value: 180, organic value: 540, IOB value: 0.33), ethylene glycol palmitate (inorganic value: 160, organic value: 360, IOB value: 0.44), methyl castor oil fatty acid (inorganic value: 162, organic value: 380, IOB value: 0.43), myristyl alcohol (inorganic value: 100, organic value: 280, IOB value: 0.36), ethylene glycol monooleate (inorganic value: 162, organic value: 400, IOB value: 0.41), ethylene glycol monostearate (inorganic value: 160, organic value: 400, IOB value: 0.4), propylene glycol monostearate (inorganic value: 160, organic value: 420, IOB value: 0.38), coconut oil alcohol (inorganic value: 100, organic value: 240, IOB value: 0.42), lauryl alcohol (inorganic value: 100, organic value: 240, IOB value: 0.42), octyldodecyl lactate (inorganic value: 160, organic value: 450, IOB value: 0.36), oleyl lactate (inorganic value: 162, organic value: 420, IOB value: 0.39) and cetyl lactate (inorganic value: 160, organic value: 380, IOB value: 0.42).

[25] The oil-in-water emulsion composition according to any one of [1] and [3] to [24] or the production method according to any one of [2] and [3] to [24], containing 0.05 to 30 mass % of the oily component based on the total amount of the composition.

[26] The oil-in-water emulsion composition according to any one of [1] and [3] to [25] or the production method according to any one of [2] and [3] to [25], containing 1 to 20 mass % of the oily component based on the total amount of the composition.

[27] The oil-in-water emulsion composition according to any one of [1] and [3] to [26] or the production method according to any one of [2] and [3] to [26], wherein the oil-in-water emulsion composition contains an oily component having an inorganic value of 1500 or less, an organic value of 3000 or less and an IOB value of 0.3 to 0.5, contains 0.05 to 20 mass % of a polyoxyethylene alkyl or alkenyl ether having alkyl group or alkenyl group has 21 to 23 carbon atoms and an average molar number of ethylene oxide added of 1.5 to 3 as the component (A) based on the total amount of the composition, and contains the component (B) at a mass ratio of the component (B) to the component (A) of 1 to 35.

[28] The oil-in-water emulsion composition according to any one of [1] and [3] to [27] or the production method according to any one of [2] and [3] to [27], wherein the oil-in-water emulsion composition contains an oily component having an inorganic value of 100 to 300, an organic value of 200 to 700 and an IOB value of 0.3 to 0.5, contains 0.1 to 10 mass % of a polyoxyethylene alkyl or alkenyl ether having alkyl group or alkenyl group having 21 to 23 carbon atoms and an average number of moles of ethylene oxide added of 1.5 to 2.5 as the component (A) based on the total amount of the composition, and contains the component (B) at a mass ratio of the component (B) to the component (A) of 1 to 20.

[29] The production method according to any one of [2] and [3] to [28], wherein the oil-in-water emulsion composition containing the water-soluble polymer is formed at 50 to 80° C.

[30] The production method according to any one of [2] and [3] to [29], wherein the composition containing the components (A) and (B) is produced by heating and mixing.

[31] The production method according to any one of [2] and [3] to [30], wherein the composition containing the components (A) and (B) is mixed with the oil-in-water emulsion composition at a temperature of 35 to 45° C.

Next, the constitution of the present invention will be described.

The oil-in-water emulsion composition in the present invention is an emulsion composition whose continuous phase is a phase containing water, and also includes a W/O/W emulsion composition.

The oil-in-water emulsion composition of the present invention is an oil-in-water emulsion composition containing an oily component having an inorganic value of 2500 or less, an organic value of 5000 or less and an IOB value of 0.3 to 0.5, the composition containing the components (A) to (C) in the aqueous phase.

The IOB value in the present invention is an abbreviation of inorganic/organic balance, and is a value corresponding to a ratio of an inorganic value of a compound to an organic value of the compound, and an index of the degree of polarity of an organic compound. Specifically, the IOB value is represented as an inorganic value/organic value.

Here, the "inorganic values" and "organic values" are determined for various atoms or functional groups, respectively, so that the "organic value" is 20 for one carbon atom in the molecule and the "inorganic value" is 100 for one hydroxyl group in the molecule, for example. The IOB value of an organic compound is calculated by integrating the "inorganic values" and "organic values" of all atoms and functional groups in the organic compound (see e.g., Yoshio Koda, Yuki Gainenzu: Kiso to Oyo [Organic Conceptual Diagram: Basis and Application], pp. 11-17, Sankyo Publishing Co., Ltd., 1984).

In the present invention, when an oily component having an inorganic value of 2500 or less, an organic value of 5000 or less and an IOB value of 0.3 to 0.5 is used, the polyoxyethylene alkyl or alkenyl ether (A) tends to be easily dissolved in the oily component and the water-evaporation-inhibiting effect of the aqueous phase tends to be decreased. In particular, the tendency is great when an oily component having an inorganic value of 1500 or less, an organic value of 3000 or less and an IOB value of 0.3 to 0.5 is used, and the tendency is significant when an oily component having an inorganic value of 100 to 300, an organic value of 200 to 700 and an IOB value of 0.3 to 0.5 is used.

Specific examples of such oily components include propylene glycol isostearate (inorganic value: 166, organic value: 410, IOB value: 0.4), propylene glycol oleate (inorganic value: 162, organic value: 420, IOB value: 0.39), ethylene glycol dioctanoate (inorganic value: 120, organic value: 340, IOB value: 0.35), diethylene glycol dicaprate (inorganic value: 195, organic value: 480, IOB value: 0.41), propylene glycol dicaproate (inorganic value: 120, organic value: 300, IOB value: 0.4), glyceryl dimyristate (inorganic value: 220, organic value: 620, IOB value: 0.35), glyceryl di(coconut oil fatty acid) (inorganic value: 220, organic value: 540, IOB value: 0.41), glyceryl dilaurate (inorganic value: 220, organic value: 540, IOB value: 0.41), diethylene glycol dilaurate (inorganic value: 195, organic value: 560, IOB value: 0.35), polyethylene glycol dilaurate (inorganic value: 270, organic value: 600, IOB value: 0.45), glyceryl monostearate diacetate (inorganic value: 180, organic value: 500, IOB value: 0.36), glyceryl sesquioleate (inorganic value: 243, organic value: 600, IOB value: 0.41), diisopropyl sebacate (inorganic value: 120, organic value: 300, IOB value: 0.4), diethyl sebacate (inorganic value: 120, organic value: 280, IOB value: 0.43), glyceryl tri(caprylate/caprate) (inorganic value: 180, organic value: 540, IOB value: 0.33), glyceryl tri(2-ethylhexanoate) (inorganic value: 180, organic value: 510, IOB value: 0.35), trimethylolpropane trioctanoate (inorganic value: 180, organic value: 550, IOB value: 0.33), glyceryl tricaprylate (inorganic value: 180, organic value: 540, IOB value: 0.33), ethylene glycol palmitate (inorganic value: 160, organic value: 360, IOB value: 0.44), methyl castor oil fatty acid (inorganic value: 162, organic value: 380, IOB value: 0.43), myristyl alcohol (inorganic value: 100, organic value: 280, IOB value: 0.36), ethylene glycol monooleate (inorganic value: 162, organic value: 400, IOB value: 0.41), ethylene glycol monostearate (inorganic value: 160, organic value: 400, IOB value: 0.4), propylene glycol monostearate (inorganic value: 160, organic value: 420, IOB value: 0.38), coconut oil alcohol (inorganic value: 100, organic value: 240, IOB value: 0.42), lauryl alcohol (inorganic value: 100, organic value: 240, IOB value: 0.42), octyldodecyl lactate (inorganic value: 160, organic value: 450, IOB value: 0.36), oleyl lactate (inorganic value: 162, organic value: 420, IOB value: 0.39) and cetyl lactate (inorganic value: 160, organic value: 380, IOB value: 0.42).

If the content of such an oily component is 0.05 mass % or more based on the total amount of the composition, the water-evaporation-inhibiting effect tends to be decreased. In particular, if the content is 1 mass % or more, the tendency is great.

The upper limit of the content of such an oily component in the oil-in-water emulsion composition of the present invention is not limited, insofar as an oil-in-water emulsion system can be formed, but is preferably 30 mass % or less, more preferably 20 mass % or less.

In the polyoxyethylene alkyl or alkenyl ether (A) used in the present invention (hereinafter sometimes called polyoxyethylene alkyl ether (A) or POE alkyl ether), the alkyl group or alkenyl group has 20 to 24 carbon atoms and an average molar number of ethylene oxide added of 1.5 to 4.

The alkyl group or alkenyl group in the polyoxyethylene alkyl ether (A) may be linear or branched and may have any structure, but is preferably a linear or branched alkyl group, more preferably a linear alkyl group. The alkyl group or alkenyl group has 20 to 24 carbon atoms, preferably 21 to 23 carbon atoms, and is even more preferably a behenyl group having 22 carbon atoms. An alkyl group or alkenyl group having less than 20 carbon atoms is not preferred, because the water-evaporation-inhibiting effect is inferior. An alkyl group or alkenyl group having more than 24 carbon atoms is not preferred for formulation, because the component is poorly soluble in an aqueous phase.

The average molar number of ethylene oxide added in the polyoxyethylene alkyl ether (A) is in the range of 1.5 to 4, preferably 1.5 to 3, more preferably 1.5 to 2.5. An average molar number of ethylene oxide added of less than 1.5 is not preferred, because the component is highly crystalline and is poorly soluble in the aqueous phase. An average molar number of ethylene oxide added of more than 4 is not preferred, because the water-evaporation-inhibiting effect is significantly decreased. Commonly available polyoxyethylene alkyl ethers (A) are mixtures of polyoxyethylene alkyl ethers in which the number of moles of ethylene oxide added is very widely distributed around the desired degree of polymerization, but it is important in the present invention that they have an average molar number of ethylene oxide added within the above range.

Examples of the polyoxyethylene alkyl ether (A) of the present invention include polyoxyethylene (2) arachyl ether, polyoxyethylene (3) arachyl ether, polyoxyethylene (4) arachyl ether, polyoxyethylene (2) behenyl ether, polyoxyethylene (3) behenyl ether, polyoxyethylene (4) behenyl ether, polyoxyethylene (2) carnaubyl ether, polyoxyethylene (3) carnaubyl ether and polyoxyethylene (4) carnaubyl ether. Preferred examples include polyoxyethylene (2) behenyl ether, polyoxyethylene (3) behenyl ether and polyoxyethylene (4) behenyl ether. Polyoxyethylene alkyl ethers other than those examples may also be used in combination if the average molar number of ethylene oxide added in the polyoxyethylene alkyl ether (A) used is within the above range.

The content of the polyoxyethylene alkyl ether (A) in the oil-in-water emulsion composition of the present invention is preferably 0.05 to 20 mass %, more preferably 0.1 to 20 mass %, even more 0.1 to 10 mass %, based on the total amount of the composition. If the content is within this range, it is preferable, because the water-evaporation-inhibiting effect is high and the component can be easily added to the aqueous phase.

Examples of the polyol (B) used in the present invention include a glycol such as ethylene glycol, diethylene glycol, triethylene glycol, polyethylene glycol (average molecular mass: less than 650), propylene glycol, dipropylene glycol, polypropylene glycol (average molecular mass: less than 650), isoprene glycol and 1,3-butylene glycol; glycerin, diglycerin and polyglycerin. Such polyols may be used singly or in a combination of two or more as appropriate.

Among them, ethylene glycol, diethylene glycol, propylene glycol, dipropylene glycol and 1,3-butylene glycol may be suitably used, and dipropylene glycol is more preferred, particularly in terms of solubility and usability of the polyoxyethylene alkyl ether (A) of the present invention.

The polyol is preferably contained in combination with the polyoxyethylene alkyl ether (A) at a mass ratio of the polyol to the component (A) of 0.5 to 50, more preferably 1 to 35, even more preferably 1 to 20. If the mass ratio is within this range, it is preferable, because solubility of the polyoxyethylene alkyl ether (A) is good and a good water-evaporation-inhibiting effect is provided.

The water-soluble polymer (C) is used in the oil-in-water emulsion composition of the present invention. The water-soluble polymer disperses and maintains the polyoxyethylene alkyl ether (A) in the aqueous phase stably and contributes to the water-evaporation-inhibiting effect. If the polyoxyethylene alkyl ether (A) can be dispersed and maintained in the aqueous phase stably, various water-soluble polymers may be selected according to the formulation used.

Examples of the water-soluble polymer used in the present invention include water-soluble cationic polymers, anionic polymers, nonionic polymers, and amphoteric polymers or dipolar polymers.

Specific examples of cationic polymers include poly(dimethyldiallylammonium halide) cationic polymers, or dimethyldiallylammonium halide-acrylamide copolymer cationic polymers, or quaternary nitrogen-containing cellulose ethers, or condensation products of polyethylene glycol, epichlorohydrin, propyleneamine, and tallowylamine obtained from tallow fatty acid, or cationized vinylpyrrolidone-dimethylaminoethyl methacrylate copolymers. Poly(dimethyldiallylammonium halide) cationic polymers include those marketed under the trade name MERQUAT® 100 by Merck & Co., Inc., United States. Dimethyldiallylammonium halide-acrylamide copolymer cationic polymers include MERQUAT® 550[Merck & Co., Inc., United States]. Examples of condensation products of polyethylene glycol, epichlorohydrin, propyleneamine, and tallowylamine or cocoylamine include those marketed under the trade name POLYQUAT® H by Henkel International Co., Germany. Quaternary nitrogen-containing cellulose ethers include those marketed under the trade names POLYMER® JR-400, POLYMER® JR-125 and POLYMER® JR-30M by Union Carbide Corp., United States. Cationized vinylpyrrolidone-dimethylaminoethyl methacrylate copolymers included those marketed under the trade names GAFQUAT® 755 and GAFQUAT® 734 by GAF Corp., United States.

Specific examples of anionic polymers include carboxyvinyl polymers, carboxymethylcellulose, carageenan, xanthan gum, polystyrene sulfonate, agar, ghatti gum, karaya gum, pectin and alginate salts, poly(acrylic acid) and acrylic acid and methacrylic acid derivatives such as alkali metal and ammonium salts of acrylic acid and methacrylic acid.

Specific examples of nonionic polymers include cellulose ethers (such as hydroxybutylmethylcellulose, hydroxypropylcellulose, hydroxypropylmethylcellulose, ethylhydroxyethylcellulose and hydroxyethylcellulose), propylene glycol alginate, polyacrylamide, a (sodium acrylate/sodium acryloyldimethyltaurate) copolymer, poly(ethylene oxide), polyvinyl alcohol, polyvinylpyrrolidone, hydroxypropyl guar gum, locust bean gum, amylose, hydroxyethylamylose, hyaluronic acid and its alkali metal salts, starch and starch derivatives, and mixtures thereof.

Specific examples of amphoteric polymers or dipolar polymers include an octylacrylamide/acrylate/butylaminoethyl methacrylate copolymer, POLYQUATERNIUM®-47 and POLYQUATERNIUM®-43.

Such water-soluble polymers can be used singly or in a combination of two or more as appropriate. Carboxyvinyl polymers, an alkyl acrylate-methacrylate copolymer, xanthan gum, hydroxypropylmethylcellulose, polyacrylamide, a (sodium acrylate/sodium acryloyldimethyltaurate) copolymer, and hyaluronic acid and its alkali metal salts are preferred, because they can be readily applied to various formulations.

The content of the water-soluble polymer used in the present invention is preferably 0.01 to 5 mass %, more preferably 0.05 to 3 mass %, based on the total amount of the composition. If the content is within this range, it is preferable, because stability of formulation is maintained and a superior water-evaporation-inhibiting effect is provided.

The oil-in-water emulsion compositions of the present invention may contain, in addition to the above essential components, higher alcohols, fatty acids, esters, sterols, sterol fatty acid esters, hydrocarbons, fats and oils, silicone oils, moisturizers, plant extracts, vitamins, antioxidants, antimicrobial antiseptic agents, antiphlogistics, insect repellents, physiologically active ingredients, salts, chelators, neutralizers, pH adjusters and flavors without departing from the purpose of the present invention.

Formulations of the oil-in-water emulsion compositions of the present invention are not particularly limited, and they are prepared into liquids, emulsions, gels, sprays, mousses and the like.

Applications of the oil-in-water emulsion compositions of the present invention are not particularly limited, and they may be suitably used for cosmetics, drugs, quasi drugs and the like. Specifically, the compositions can be suitably used as hair cosmetics such as shampoos, rinses and conditioners; skin cosmetics such as face washes, cleansing cosmetics, lotions, milks, beauty creams, make up bases, sunscreen cosmetics, packs and massage cosmetics; and external pharmaceuticals such as ointments and creams containing various agents. In particular, the oil-in-water emulsion compositions of the present invention are preferably used as preparations for external use on skin which are not washed off and retained in the skin, because they have a high moisture retention effect.

The oil-in-water emulsion composition of the present invention can have a high water-evaporation-inhibiting effect and high stability over time by containing the components (A) to (C) in the aqueous phase.

However, the polyoxyethylene alkyl ether (A) is easily dissolved in an oily component having an inorganic value of 2500 or less, an organic value of 5000 or less and an IOB value of 0.3 to 0.5, so that the polyoxyethylene alkyl ether (A) is dissolved in the oily phase, resulting in a significant decrease in the water-evaporation-inhibiting effect of the aqueous phase, when the polyoxyethylene alkyl ether (A) is mixed with a specific oily component at a high temperature (60° C. or more) in emulsification such as common phase inversion emulsification (such as reversal emulsification or phase inversion temperature emulsification) or non-phase inversion emulsification.

Accordingly, in the present invention, the polyoxyethylene alkyl ether (A) may be stably added to the aqueous phase and a good moisture evaporation suppressing effect and good stability over time can be provided by previously forming an oil-in-water emulsion composition containing the water-soluble polymer, and then mixing a composition containing the components (A) and (B) with the oil-in-water emulsion composition at a temperature of 45° C. or less.

The previously formed oil-in-water emulsion composition containing the water-soluble polymer may be produced using various formation methods such as dispersion (a method of emulsification using a rotary stirring emulsification apparatus or a membrane emulsification apparatus), phase transfer emulsification (such as reversal emulsification or phase inversion temperature emulsification) and self-emulsification (a method of emulsification without application of mechanical or thermal energy from the outside). This oil-in-water emulsion composition containing the water-soluble polymer may be formed by heating to 50 to 80° C. as necessary.

On the other hand, the composition containing the components (A) and (B) is made homogeneous by heating and mixing, preferably by heating to 50 to 80° C.

This composition containing the components (A) and (B) is mixed with the previously formed oil-in-water emulsion composition preferably at a temperature of 45° C. or less, more preferably at a temperature of 35 to 45° C. The polyoxyethylene alkyl ether (A) can be stably added to the aqueous phase if the temperature during mixing is within this range. The temperatures before mixing of the respective compositions are not limited if the temperature during mixing is within this range. However, the composition containing the components (A) and (B) is preferably mixed with the previously formed oil-in-water emulsion composition at approximately equal temperatures to make the temperature control easier.

EXAMPLES

The present invention will be more specifically described below with reference to examples and comparative examples, however, the present invention is not limited to the following examples. The amount of each component is represented by mass %.

[Test 1] Water-Evaporation-Inhibiting Effect

Five gram of the components in each of Examples 1 to 7, Comparative Examples 1 to 3 and Reference Examples 1 to 4 as shown in the following Tables 1 to 4, and the following control, was added to a petri dish having an opening area of 13.85 cm$^2$, and the change in weight of the sample at a humidity of 30% and a temperature of 30° C. was measured after 1, 3, 5, 7, 12, 18 and 24 hours. The gradient of change in weight was plotted as an absolute value with n in (nX+m; where X is time h) calculated by least-squares analysis as the water evaporation rate (unit: mg/h). The water evaporation rate was determined as an average of three measurements in total for each sample.

The water evaporation inhibition ratio defined below was calculated from the water evaporation rate. The higher the water evaporation inhibition ratio, the higher the degree of inhibition of water evaporation. The results are collectively described in Tables 1 to 4.

Moisture evaporation suppression ratio (%)={1−(water evaporation rate in Example or Comparative Example)/(water evaporation rate in control)}×100

[Control]

| Components | Content (%) |
|---|---|
| Dipropylene glycol | 10 |
| 2% carboxyvinyl polymer (SYNTHALEN® K, manufactured by Wako Pure Chemical Industries, Ltd.) | 7.5 |
| 10% potassium hydroxide | 0.7 |
| Disodium edetate | 0.03 |
| Phenoxyethanol | 0.35 |
| Pure water | balance |

TABLE 1

Low-temperature addition

| | Component | IOB value | Example 1a | Example 1b | Example 1c | Example 2a | Example 2b | Example 2c | Example 3a | Example 3b | Example 3c | Example 4a | Example 4b | Example 4c |
|---|---|---|---|---|---|---|---|---|---|---|---|---|---|---|
| 1 | Polyoxyethylene (2) behenyl ether | | 0.2 | 0.3 | 0.4 | 0.2 | 0.3 | 0.4 | 0.2 | 0.3 | 0.4 | 0.2 | 0.3 | 0.4 |
| 2 | Dipropylene glycol | | 10 | 10 | 10 | 10 | 10 | 10 | 10 | 10 | 10 | 10 | 10 | 10 |
| 3 | Propylene glycol isostearate | 0.4 | 5 | 5 | 5 | | | | | | | | | |
| 4 | Diisopropyl sebacate | 0.43 | | | | 5 | 5 | 5 | | | | | | |
| 5 | Diethyl sebacate | 0.4 | | | | | | | 5 | 5 | 5 | | | |
| 6 | Octyldodecyl myristate | 0.09 | | | | | | | | | | 5 | 5 | 5 |
| 7 | Mineral oil | 0 | | | | | | | | | | | | |
| 8 | Squalane | 0 | | | | | | | | | | | | |
| 9 | Dimethylpolysiloxane | 0.4 | | | | | | | | | | | | |
| 10 | PEG-60 hydrogenated castor oil | | 0.2 | 0.2 | 0.2 | 0.2 | 0.2 | 0.2 | 0.2 | 0.2 | 0.2 | 0.2 | 0.2 | 0.2 |
| 11 | 2% carboxyvinyl polymer *1 | | 7.5 | 7.5 | 7.5 | 7.5 | 7.5 | 7.5 | 7.5 | 7.5 | 7.5 | 7.5 | 7.5 | 7.5 |
| 12 | 10% potassium hydroxide | | 0.7 | 0.7 | 0.7 | 0.7 | 0.7 | 0.7 | 0.7 | 0.7 | 0.7 | 0.7 | 0.7 | 0.7 |
| 13 | Disodium edetate | | 0.03 | 0.03 | 0.03 | 0.03 | 0.03 | 0.03 | 0.03 | 0.03 | 0.03 | 0.03 | 0.03 | 0.03 |
| 14 | Pure water | | Balance | Balance | Balance | Balance | Balance | Balance | Balance | Balance | Balance | Balance | Balance | Balance |
| 15 | Phenoxyethanol | | 0.35 | 0.35 | 0.35 | 0.35 | 0.35 | 0.35 | 0.35 | 0.35 | 0.35 | 0.35 | 0.35 | 0.35 |
| | Water-evaporation-inhibition ratio (%) | | 40.4 | 72.5 | 79.4 | 86.4 | 86.4 | 83.4 | 78.7 | 83 | 85.1 | 78.4 | 79.6 | 80 |

TABLE 2

Low-temperature addition

| Component | IOB value | Example 5a | Example 5b | Example 5c | Example 6a | Example 6b | Example 6c | Example 7a | Example 7b | Example 7c |
|---|---|---|---|---|---|---|---|---|---|---|
| 1 Polyoxyethylene (2) behenyl ether | | 0.2 | 0.3 | 0.4 | 0.2 | 0.3 | 0.4 | 0.2 | 0.3 | 0.4 |
| 2 Dipropylene glycol | | 10 | 10 | 10 | 10 | 10 | 10 | 10 | 10 | 10 |
| 3 Propylene glycol isostearate | 0.4 | | | | | | | | | |
| 4 Diisopropyl sebacate | 0.43 | | | | | | | | | |
| 5 Diethyl sebacate | 0.4 | | | | | | | | | |
| 6 Octyldodecyl myristate | 0.09 | | | | | | | | | |
| 7 Mineral oil | 0 | 5 | 5 | 5 | | | | | | |
| 8 Squalane | 0 | | | | 5 | 5 | 5 | | | |
| 9 Dimethylpolysiloxane | 0.4 | | | | | | | 5 | 5 | 5 |
| 10 PEG-60 hydrogenated castor oil | | 0.2 | 0.2 | 0.2 | 0.2 | 0.2 | 0.2 | 0.2 | 0.2 | 0.2 |
| 11 2% carboxyvinyl polymer *1 | | 7.5 | 7.5 | 7.5 | 7.5 | 7.5 | 7.5 | 7.5 | 7.5 | 7.5 |
| 12 10% potassium hydroxide | | 0.7 | 0.7 | 0.7 | 0.7 | 0.7 | 0.7 | 0.7 | 0.7 | 0.7 |
| 13 Disodium edetate | | 0.03 | 0.03 | 0.03 | 0.03 | 0.03 | 0.03 | 0.03 | 0.03 | 0.03 |
| 14 Pure water | | Balance | Balance | Balance | Balance | Balance | Balance | Balance | Balance | Balance |
| 15 Phenoxyethanol | | 0.35 | 0.35 | 0.35 | 0.35 | 0.35 | 0.35 | 0.35 | 0.35 | 0.35 |
| Water-evaporation-inhibition ratio (%) | | 82 | 82 | 81 | 82.4 | 82.8 | 82.8 | 84.4 | 84.3 | 85.4 |

TABLE 3

High-temperature addition

| Component | IOB value | Comparative Example 1a | Comparative Example 1b | Comparative Example 1c | Comparative Example 2a | Comparative Example 2b | Comparative Example 2c | Comparative Example 3a | Comparative Example 3b | Comparative Example 3c | Reference Example 1a | Reference Example 1b | Reference Example 1c |
|---|---|---|---|---|---|---|---|---|---|---|---|---|---|
| 1 Polyoxyethylene (2) behenyl ether | | 0.2 | 0.3 | 0.4 | 0.2 | 0.3 | 0.4 | 0.2 | 0.3 | 0.4 | 0.2 | 0.3 | 0.4 |
| 2 Propylene glycol isostearate | 0.4 | 5 | 5 | 5 | | | | | | | | | |
| 3 Diisopropyl sebacate | 0.43 | | | | 5 | 5 | 5 | | | | | | |
| 4 Diethyl sebacate | 0.4 | | | | | | | 5 | 5 | 5 | | | |
| 5 Octyldodecyl myristate | 0.09 | | | | | | | | | | 5 | 5 | 5 |
| 6 Mineral oil | 0 | | | | | | | | | | | | |
| 7 Squalane | 0 | | | | | | | | | | | | |
| 8 Dimethylpolysiloxane | 0.4 | | | | | | | | | | | | |
| 9 PEG-60 hydrogenated castor oil | | 0.2 | 0.2 | 0.2 | 0.2 | 0.2 | 0.2 | 0.2 | 0.2 | 0.2 | 0.2 | 0.2 | 0.2 |
| 10 2% carboxyvinyl polymer *1 | | 7.5 | 7.5 | 7.5 | 7.5 | 7.5 | 7.5 | 7.5 | 7.5 | 7.5 | 7.5 | 7.5 | 7.5 |
| 11 10% potassium hydroxide | | 0.7 | 0.7 | 0.7 | 0.7 | 0.7 | 0.7 | 0.7 | 0.7 | 0.7 | 0.7 | 0.7 | 0.7 |
| 12 Disodium edetate | | 0.03 | 0.03 | 0.03 | 0.03 | 0.03 | 0.03 | 0.03 | 0.03 | 0.03 | 0.03 | 0.03 | 0.03 |
| 13 Dipropylene glycol | | 10 | 10 | 10 | 10 | 10 | 10 | 10 | 10 | 10 | 10 | 10 | 10 |
| 14 Pure water | | Balance | Balance | Balance | Balance | Balance | Balance | Balance | Balance | Balance | Balance | Balance | Balance |
| 15 Phenoxyethanol | | 0.35 | 0.35 | 0.35 | 0.35 | 0.35 | 0.35 | 0.35 | 0.35 | 0.35 | 0.35 | 0.35 | 0.35 |
| Water-evaporation-inhibition ratio (%) | | 21.6 | 54.9 | 70.6 | 6.4 | 7.3 | 22.7 | 10.6 | 8.5 | 6.4 | 80 | 80.8 | 80 |

TABLE 4

| | | High-temperature addition | | | | | | | | |
|---|---|---|---|---|---|---|---|---|---|---|
| Component | IOB value | Reference Example 2a | Reference Example 2b | Reference Example 2c | Reference Example 3a | Reference Example 3b | Reference Example 3c | Reference Example 4a | Reference Example 4b | Reference Example 4c |
| 1 Polyoxyethylene (2) behenyl ether | | 0.2 | 0.3 | 0.4 | 0.2 | 0.3 | 0.4 | 0.2 | 0.3 | 0.4 |
| 2 Propylene glycol isostearate | 0.4 | | | | | | | | | |
| 3 Diisopropyl sebacate | 0.43 | | | | | | | | | |
| 4 Diethyl sebacate | 0.4 | | | | | | | | | |
| 5 Octyldodecyl myristate | 0.09 | | | | | | | | | |
| 6 Mineral oil | 0 | 5 | 5 | 5 | | | | | | |
| 7 Squalane | 0 | | | | 5 | 5 | 5 | | | |
| 8 Dimethylpolysiloxane | 0.4 | | | | | | | 5 | 5 | 5 |
| 9 PEG-60 hydrogenated castor oil | | 0.2 | 0.2 | 0.2 | 0.2 | 0.2 | 0.2 | 0.2 | 0.2 | 0.2 |
| 10 2% carboxyvinyl polymer *1 | | 7.5 | 7.5 | 7.5 | 7.5 | 7.5 | 7.5 | 7.5 | 7.5 | 7.5 |
| 11 10% potassium hydroxide | | 0.7 | 0.7 | 0.7 | 0.7 | 0.7 | 0.7 | 0.7 | 0.7 | 0.7 |
| 12 Disodium edetate | | 0.03 | 0.03 | 0.03 | 0.03 | 0.03 | 0.03 | 0.03 | 0.03 | 0.03 |
| 13 Dipropylene glycol | | 10 | 10 | 10 | 10 | 10 | 10 | 10 | 10 | 10 |
| 14 Pure water | | Balance | Balance | Balance | Balance | Balance | Balance | Balance | Balance | Balance |
| 15 Phenoxyethanol | | 0.35 | 0.35 | 0.35 | 0.35 | 0.35 | 0.35 | 0.35 | 0.35 | 0.35 |
| Water-evaporation-inhibition ratio (%) | | 82.5 | 82.5 | 82.5 | 79.9 | 82.2 | 82.2 | 84.9 | 85.4 | 84.2 |

(Production Method 1: Low-Temperature Addition of POE Behenyl Ether)
(1) The components 1 and 2 are heated to 60° C. and homogeneously mixed.
(2) The components 3 to 10 are homogeneously mixed at 80° C.
(3) The components 11 to 14 are homogeneously mixed at 80° C.
(4) The components (3) are gradually added to the components (2) while being maintained to be heated at 80° C., followed by homogeneous mixing.
(5) The components (4) are gradually cooled to 40° C., and the components (1) and the component 15 are added to the components (4) at 40° C., followed by homogeneous mixing.

(Production Method 2: High-Temperature Addition of POE Behenyl Ether)
(1) The components 1 to 9 are heated to 80° C. and homogeneously mixed.
(2) The components 10 to 14 are heated to 80° C. and homogeneously mixed.
(3) The components (2) are gradually added to the components (1) while being maintained to be heated at 80° C., followed by homogeneous mixing.
(4) The components (3) are gradually cooled to 40° C., and the component 15 is added at 40° C., followed by homogeneous mixing.

In the compositions of Comparative Examples 1 to 3 containing an oily component having an inorganic value of 2500 or less, an organic value of 5000 or less and an IOB value of 0.3 to 0.5, the polyoxyethylene alkyl ether (A) was dissolved in the oily component and the water-evaporation-inhibiting effect was significantly decreased. On the other hand, the compositions of Examples 1 to 7 containing the polyoxyethylene alkyl ether (A) and the water-soluble polymer (B) in the aqueous phase exhibited a water-evaporation-inhibiting effect superior to those of oil-in-water emulsion compositions.

In the compositions of Reference Examples 1 to 4 using an oily component other than an oily component having an inorganic value of 2500 or less, an organic value of 5000 or less and an IOB value of 0.3 to 0.5, no marked decrease in water-evaporation-inhibiting effect was observed, because the polyoxyethylene alkyl ether (A) was not dissolved in the oily component and was dispersed in the aqueous phase.

The invention claimed is:

1. A method for producing an oil-in-water emulsion composition, wherein the oil-in-water emulsion composition comprises an oily component having an inorganic value of 2500 or less, an organic value of 5000 or less, and an IOB value of from 0.3 to 0.5 as the oily component in an oil phase,
   the method comprising forming an oil-in-water emulsion composition comprising a water-soluble polymer (C), followed by mixing a composition comprising the following components (A) and (B) with the oil-in-water emulsion composition comprising the at least one water-soluble polymer (C) at a temperature of 45° C. or less:
   (A) a polyoxyethylene alkyl or alkenyl ether having an alkyl group or an alkenyl group having from 20 to 24 carbon atoms and an added average molar number of ethylene oxide of from 1.5 to 4; and
   (B) a polyol.

2. The method according to claim 1, wherein the mixing temperature is from 35 to 45° C.

3. The method according to claim 1, wherein the oily component has an inorganic value of 1500 or less, an organic value of 3000 or less and an IOB value of from 0.3 to 0.5.

4. The method according to claim 1, wherein the oily component has an inorganic value of 100 to 300, an organic value of 200 to 700 and an IOB value of from 0.3 to 0.5.

5. The method according to claim 1, wherein the oily component is present in an amount of from 0.05 to 30 mass % based on the total amount of the composition.

6. The method according to claim 1, wherein in the component (A) the added average molar number of ethylene oxide is from 1.5 to 3.

7. The method according to claim 1, wherein the component (A) is present in an amount of from 0.05 to 20 mass % based on the total amount of the composition.

8. The method according to claim 1, wherein the component (B) is at least one member selected from the group consisting of a glycol, glycerin, diglycerin, and polyglycerin.

9. The method according to claim 1, wherein the component (B) is at least one member selected from the group consisting of ethylene glycol, diethylene glycol, triethylene glycol, an polyethylene glycol having an average molecular mass of less than 650, propylene glycol, dipropylene glycol, a polypropylene glycol having an average molecular mass of less than 650, isoprene glycol, 1,3-butylene glycol, glycerin, diglycerin and polyglycerin.

10. The method according to claim 1, wherein a mass ratio of the component (B) to the component (A) is from 0.5 to 50.

11. The method according to claim 1, wherein the water-soluble polymer (C) is at least one member selected from the group consisting of a carboxyvinyl polymer, an alkyl acrylate-methacrylate copolymer, xanthan gum, hydroxypropylmethylcellulose, polyacrylamide, and a (sodium acrylate/sodium acryloyldimethyltaurate) copolymer.

12. The method according to claim 1, wherein the water-soluble polymer (C) is present in an amount of from 0.01 to 5 mass % based on the total amount of the composition.

13. An oil-in-water emulsion composition comprising an oily component having an inorganic value of 2500 or less, an organic value of 5000 or less and an IOB value of from 0.3 to 0.5, wherein the oily component present in an amount of 0.05 mass % or more based on the total amount of the composition, and the oil-in-water emulsion composition comprises the following components (A), (B), and (C) in an aqueous phase:

(A) a polyoxyethylene alkyl or alkenyl ether having an alkyl group or an alkenyl group having from 20 to 24 carbon atoms and an added average molar number of ethylene oxide of from 1.5 to 4;

(B) a polyol; and (C) a water-soluble polymer.

14. A method for inhibiting water evaporation from an oil-in-water emulsion composition, comprising:

adding the following components (A), (B), and (C) to an aqueous phase of an oil-in-water emulsion:

(A) a polyoxyethylene alkyl or alkenyl ether having an alkyl group or an alkenyl group having from 20 to 24 carbon atoms and an added average molar number of ethylene oxide of from 1.5 to 4;

(B) a polyol; and (C) a water-soluble polymer, thereby obtaining the oil-in-water emulsion composition comprising an oily component having an inorganic value of 2500 or less, an organic value of 5000 or less and an IOB value of from 0.3 to 0.5, wherein the oily component present in an amount of 0.05 mass % or more based on the total amount of the composition, and the oil-in-water emulsion composition comprises the components (A) to (C) in the aqueous phase.

\* \* \* \* \*